United States Patent [19]
Bacehowski et al.

[11] Patent Number: 5,217,426
[45] Date of Patent: * Jun. 8, 1993

[54] COMBINATION DISPOSABLE PLASTIC BLOOD RECEIVING CONTAINER AND BLOOD COMPONENT CENTRIFUGE

[75] Inventors: David V. Bacehowski, Wildwood, Ill.; Herbert M. Cullis, Silver Spring, Md.; Armand R. VanBaelen, Rolling Meadows, Ill.

[73] Assignee: Baxter International Inc., Deerfield, Ill.

[*] Notice: The portion of the term of this patent subsequent to Jun. 19, 2007 has been disclaimed.

[21] Appl. No.: 744,947

[22] Filed: Aug. 14, 1991

Related U.S. Application Data

[60] Continuation of Ser. No. 660,710, Feb. 25, 1991, abandoned, which is a division of Ser. No. 463,694, Jan. 11, 1990, Pat. No. 5,006,103, which is a division of Ser. No. 824,182, Aug. 12, 1977, Pat. No. 4,934,995.

[51] Int. Cl.$^5$ .............................................. B04B 7/08
[52] U.S. Cl. ........................................ 494/45; 494/18
[58] Field of Search ............... 494/35, 36, 37, 45, 494/18, 1, 16, 17, 43, 85; 220/403, 404; 604/408, 410

[56] References Cited

U.S. PATENT DOCUMENTS

| | | |
|---|---|---|
| 1,472,085 | 10/1923 | Philip . |
| 1,512,469 | 10/1924 | Kellogg . |
| 1,954,676 | 8/1931 | Lindberg . |
| 2,083,899 | 6/1937 | Duerig . |
| 2,261,394 | 11/1941 | Lindgren . |
| 2,269,716 | 1/1942 | Gregg . |
| 2,321,144 | 6/1943 | Jones . |
| 2,662,687 | 12/1953 | Spross . |
| 2,719,668 | 10/1955 | Bergner . |
| 2,730,299 | 1/1956 | Kelsey . |
| 2,885,145 | 5/1959 | Danielsson et al. . |
| 2,952,258 | 9/1960 | Chandler . |
| 3,090,549 | 5/1963 | Rastgeldi . |
| 3,096,282 | 7/1963 | Trotter . |
| 3,127,342 | 3/1964 | Mitchell . |
| 3,129,175 | 4/1964 | Jones et al. . |
| 3,655,123 | 4/1972 | Judson et al. . |
| 3,672,564 | 6/1972 | Schultz et al. . |
| 3,698,626 | 10/1972 | Kotrappa et al. . |
| 3,703,984 | 11/1972 | Pruessner . |
| 3,708,110 | 1/1973 | Unger et al. . |

(List continued on next page.)

FOREIGN PATENT DOCUMENTS

| | | |
|---|---|---|
| 43693 | 11/1887 | Fed. Rep. of Germany . |
| 373493 | 5/1937 | United Kingdom . |
| 729169 | 5/1955 | United Kingdom . |
| 812115 | 4/1959 | United Kingdom . |
| 873494 | 7/1961 | United Kingdom . |
| 1336965 | 11/1973 | United Kingdom . |
| 1451859 | 10/1976 | United Kingdom . |
| 1471204 | 4/1977 | United Kingdom . |
| 1509667 | 5/1978 | United Kingdom . |
| 1511819 | 5/1978 | United Kingdom . |

OTHER PUBLICATIONS

Response to Plaintiffs' Interrogatory No. 10 regarding the '995 patent (Dated Feb. 3, 1992).
Brief of Defendant Cobe Laboratories, Inc. In Support Of Its Motion For Partial Summary Judgment of No-
(List continued on next page.)

Primary Examiner—Robert W. Jenkins
Attorney, Agent, or Firm—Bradford R. L. Price; Gary W. McFarron

[57] ABSTRACT

A blood component separating device comprises a centrifuge bowl adapted for rotation about its axis in a centrifuge. The bowl defines an outer arcuate wall plus an inner circumferential wall, spaced from the outer wall, to define a arcuate slot adapted for receiving blood components. Access tubing is adapted for communication with the slot. Preferably, an elongated, flexible, collapsible inner liner is provided in the slot. Individual access tubing also may communicate with an elongated container interior between the ends of the elongated, collapsible container. Furthermore, a portion of the slot may define the shape of an outwardly extending spiral, to provide an increasing gravitational field upon fluids therein as the fluid moves along the slot.

45 Claims, 3 Drawing Sheets

U.S. PATENT DOCUMENTS 3,724,727 4/1973 Zundel .
3,724,747 4/1973 Unger et al. .
3,737,096 6/1973 Jones et al. .
3,748,101 7/1973 Jones et al. .
3,825,175 7/1974 Sartory .
3,858,796 1/1975 Unger et al. .
3,862,715 1/1975 Remenyik .
3,955,755 5/1976 Breillatt .
3,957,197 5/1976 Sartory et al. .
3,987,961 10/1976 Sinn et al. .
4,007,871 2/1977 Jones et al. .
4,010,894 3/1977 Kellogg et al. .
4,056,224 11/1977 Lolachi .
4,069,968 1/1978 Herman .
4,086,924 5/1978 Latham .
4,091,989 5/1978 Schlutz .
4,094,461 6/1978 Kellogg et al. .
4,109,854 8/1978 Brown .
4,113,173 9/1978 Lolachi .
4,120,448 10/1978 Cullis .
4,230,263 10/1980 Westberg .
4,356,958 11/1982 Kolobow et al. .
4,387,848 6/1983 Kellogg et al. .
4,419,089 12/1983 Kolobow et al. .
4,425,112 1/1984 Ito .
4,430,072 2/1984 Kellogg et al. .
4,734,089 3/1988 Cullis .

OTHER PUBLICATIONS n-Infringement of Baxter's U.S. Pat. No. 4,934,995 (Dated Jan. 10, 1992).

Defendant Cobe's Statement of Undisputed Material Facts As To Which There Are No Genuine Issues Pursuant To Local Rule 12(m) In Support Of Cobe's Motion For Partial Summary Judgment of Non-infringement Of Baxter's U.S. Pat. No. 4,934,995 (Dated Jan. 10, 1992).

Oak Ridge National Laboratory, "Blood Cell Separator Development For In Vivo Leukapheresis: A Critical Analysis", dated Oct., 1972.

Oak Ridge National Laboratory, "Progress In Blood Cell Separator Development For In Vivo Leukapheresis", dated Jul., 1974.

Decision of Board of Appeals in U.S. Ser. No. 824,182 (dated Jan. 27, 1989).

Interference File History of Interference No. 100,210 (separately bound) no date.

Response of Cobe Laboratories, Inc. in U.S. Civil Action No. 89 C9460 (N.D. Ill.) Apr. 19, 1991.

Translation of Opposition to German Patent No. 2835307 filed on Jun. 3, 1988.

Translation of Response to Opposition to German Patent No. 2835307 filed on Dec. 30, 1988.

Translation of Decision of German Patent Office re Opposition to German Patent No. 2835307 Mar. 19, 1990.

Translation of Appeal of Decision of German Patent Office Re German Patent Patent Application No. 2835307 Feb. 6, 1991.

Information Disclosure Statement of Oct. 3, 1990 filed in Application Ser. No. 464,694 (now U.S. Pat. No. 5,006,103).

FIG. 8

COMBINATION DISPOSABLE PLASTIC BLOOD RECEIVING CONTAINER AND BLOOD COMPONENT CENTRIFUGE

This application is a continuation of U.S. application Ser. No. 660,710, filed Feb. 25, 1991 now abandoned, which is a division of U.S. application Ser. No. 463,694, filed Jan. 11, 1990, and now issued as U.S. Pat. No. 5,006,103, which is a division of U.S. application Ser. No. 824,182, filed Aug. 12, 1977, and now issued as U.S. Pat. No. 4,934,995.

BACKGROUND OF THE INVENTION

Blood components are separated from units of human blood and utilized for separate therapy in patients. For example, blood plasma may be administered without red cells. Also, the packed red cells can be administered to a patient with a minimum of plasma or other suspending solution. Furthermore, platelets or white cells may be administered as specific components. Also, platelet-poor plasma is another product from blood utilized in various forms of therapy.

The invention of this application relates to a centrifuge which can be used to obtain, for example, separate portions of platelets, plasma (including platelet-poor plasma), other white cells, and packed red cells. The device of this invention can operate to process, in a continuous operation, an unlimited amount of blood from a donor, processing the blood to separate and return the red cells to the donor, and to harvest, as desired, the white cells, platelets and plasma. The centrifuge bowl or container of this invention utilizes a radially thin, circumferential flow path for the blood and plasma being processed, to provide a long, thin circumferential flow path in which a continuous process of separation may take place. As a result of this, a sweeping action may take place over the thin, sedimented layer of the slightly heavier particles such as the blood cells, to move the slightly lighter particles (for example the white cells) downstream with respect to the red cells. This permits the use of sharply lowered G forces than is customarily used in conventional blood separation, with the slightly lighter cells being urged to move downstream more quickly than the slightly heavier red cells, to provide a more efficient cell separation.

Also, the thin, circumferential operating path provides a very short sedimentation distance, no more than the restricted width of the path. This also provides the advantage that the centrifuge bowl container of this invention has a low blood volume so that a relatively small amount of blood is removed from the donor at any one time while at the same time facilitating the sedimenting of red cells and protecting the platelets from the known, undesirable effects of high G forces in excess of one thousand Gs.

Furthermore, the device of this invention permits the accumulation of white cells and platelets during continuous operation, in which the red cells are sedimented along the circumferential path and then withdrawn for reinfusion to the patient on a continuous or repeating basis. At the same time, the white cells and/or platelets, which generally comprise less than one percent of the blood volume, can be accumulated during the operation so that large amounts of white cells and platelets can be harvested in the single operation.

The above objectives are accomplished in the apparatus of this invention with minimal shear stresses being placed on especially the white cells and platelets.

The invention of this application effectively provides an efficient, sterile means for obtaining blood components from a donor or from reservoirs on a semi-automated basis, utilizing a disposable container of novel configuration.

DESCRIPTION OF THE INVENTION

In accordance with this invention, a blood conponent separating device comprises a centrifuge bowl or chamber adapted for rotation about its axis in a centrifuge. The bowl defines an outer arcuate wall, and an inner circumferential wall spaced to define an arcuate slot, adapted for receiving blood components. The slot is adapted to contain access tubing, and aperture means in the bowl permit the access tubing to pass out of the slot for connection with an exterior member.

In accordance with this invention, a portion of the slot adjacent the aperture means defines the shape of an outwardly extending spiral. The effect of this is to provide an increasing gravitational field upon fluid therein as the fluid moves along the slot. This causes heavier particles such as blood cells to settle outwardly, and then to slide to the outward spiral end portion of the slot for collection. At the end of the spiral portion of the slot, a radially inwardly extending step portion of the slot may be provided, whereby red blood cells positioned in the slot during centrifugation may collect at the outer end of the spiral portion.

Pockets can be provided in the outer arcuate wall defining the slot, for collection of blood cells with access tubing communicating with said pocket.

Also, a portion of the slot, positioned beyond the inwardly extending portion from the spiral portion, may define a generally circular portion which is preferably positioned radially inwardly from the spiral portion, for the purpose of collecting platelets at a lower level of centrifugal force than the red cell collection portion.

A flexible, elongated, flat container or bag for blood components may be positioned in the arcuate slot with the access tubing being in communication with the container interior. The access tubing may be positioned adjacent each end of the elongated, flat container for passage of blood components through the slot within the container. Also, additional access tubing may communicate with the elongated, flat container between the ends thereof for collection of centrifuged heavier components such as red and white blood cells.

In one embodiment, the container bowl of this invention may process blood plasma to remove platelets which, upon centrifugation, collect on the outer wall. Alternatively, the bowl of this invention may be used to process whole blood to collect both red and white blood cells and platelets, with platelet-poor plasma passing out of the end of the bag positioned within the circumferential slot. The bowl may also be used to collect red blood cells alone.

Blood, plasma, or other liquid may be fed to one end of the elongated, flat bag for passage through the bag during centrifugation. The centrifuged liquid is then withdrawn from the other end of the bag, while red and white cells may be removed at various points intermediate along the container as illustrated herein.

The tubing which is connected to the spinning, elongated, flat bag may be connected to a stationary liquid source and a receptacle for processed liquid outside of the centrifuge by the use of a conventional structure making use of the principles of Adams U.S. Pat. No. 3,586,413, Khoja, et al. U.S. Pat. No. 3,986,442, and similar prior art utilizing the feature of preventing the communication tubing from being twisted by means of the precise rotational relationship described in those patents. Accordingly, a conventional centrifuge can be adapted to receive the bowl of this invention, utilizing the rotational principles for the communication tubing described in the above-cited patents, in which one set of ends of the communication tubing is spinning with the centrifuge bowl and the other ends of the tubing are stationary, and connected outside of the centrifuge to a liquid source and a receptacle for processed liquids.

Referring to the drawings.

Figure 1:
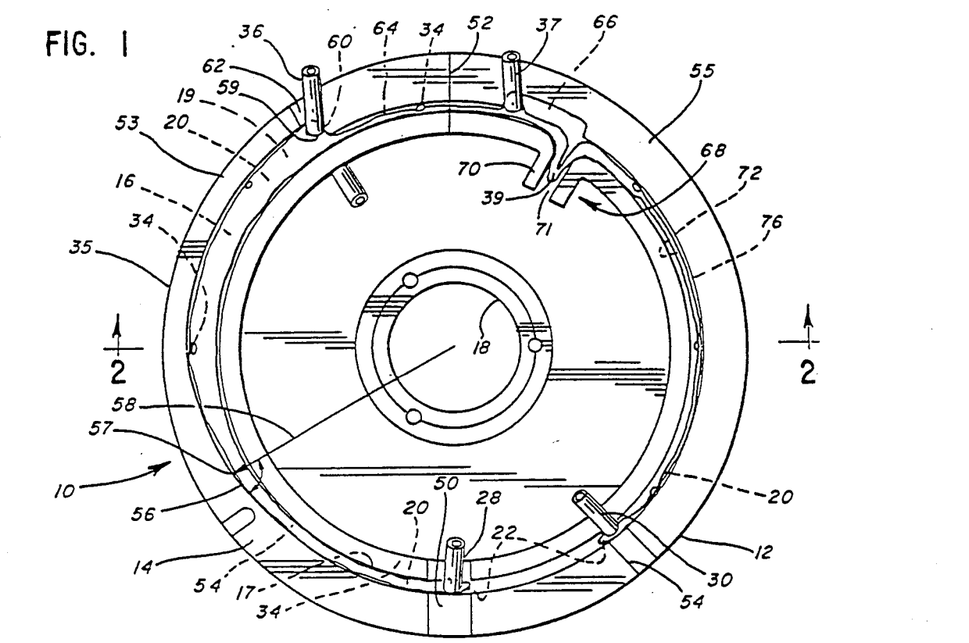
FIG. 1 is a top plan view of an embodiment of the centrifuge bowl of this invention for the collection of both red cells and platelets.
Figure 2:
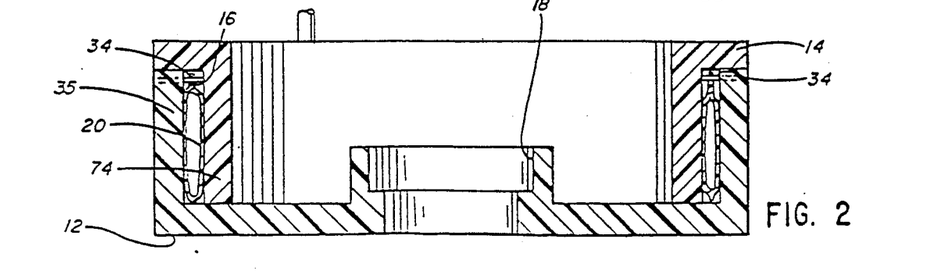
FIG. 2 is a sectional view of the centrifuge bowl of this invention, taken along line 2—2 of FIG. 1.

Referring to FIGS. 1 and 2, centrifuge bowl or container 10 is illustrated, comprising a bowl member 12 and a cover 14 which is removable from the bowl member, to define an arcuate channel or slot 16 between cover 14 and bowl member 12 as shown in FIG. 2. Typically, channel 16 may be 50 mm. high, tapering from about 3.5 to 4.5 mm. (preferably 4 mm.) in width at point 17 to about 12 mm. in width at approximately point 19, and then narrowing again. Overall, channel 16 may be about 28 inches in circumferential measurement.

As shown in FIG. 2, bowl member 12 defines a central aperture-defining sleeve 18, to permit attachment of the bowl to a centrifuge rotor for spinning of the container 10. Bowl member 12 comprises a disk-like portion which terminates in a vertical arcuate wall 35. Cover member 14 has a vertical wall portion 74 and may be seen to interfit and overlie bowl member 12. The region formed between arcuate wall 35 and arcuate wall 74 of cover member 14 defines channel 16.

Figure 3:
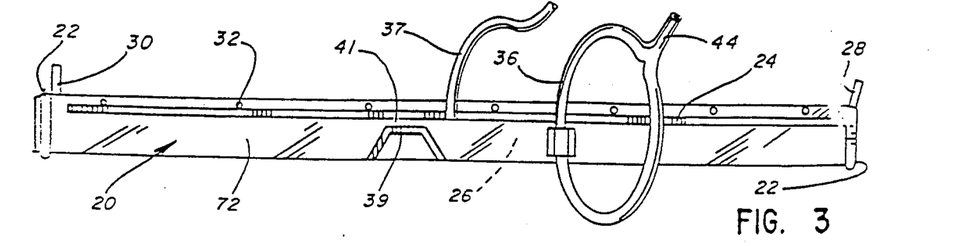
FIG. 3 is an elevational view of a flexible, elongated, flat container which may be utilized herein.
Figure 4:
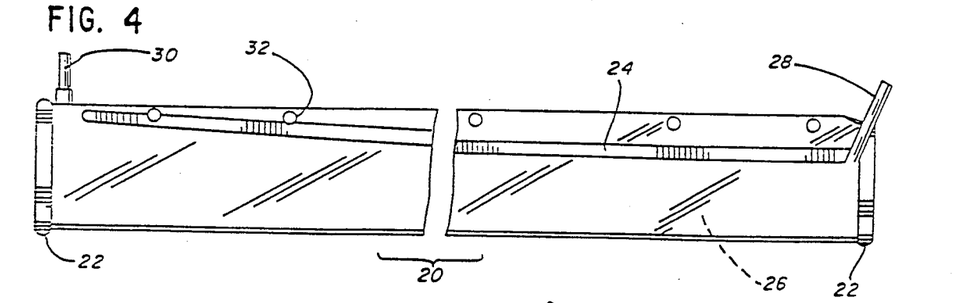
FIG. 4 is an enlarged, fragmentary elevational view of the container of FIG. 3.

Referring to FIGS. 3 and 4 a flexible, elongated flat container or bag 20 for placing in arcuate channel 16 is disclosed. Container or bag 20 may be made out of a single piece of plastic, folded into U-shaped cross section at the bottom, and sealed with R.F. (Radio Frequency) seals 22 at the ends thereof, or by any other desired sealing technique. Also, an upper R.F. seal 24 is provided to seal an interior portion 26 of the container in sterile manner from the exterior.

Tubings 28, 30 are provided at each end of the flexible, flat container or bag to serve as an inlet and an outlet, tubing 28 being typically used as the inlet and 30 as the outlet. Upper R.F. seal 24 may slope upwardly as shown for the purpose of encouraging the downstream migration of air bubbles.

In the unsealed edge portion of bag 20, a plurality of perforations 32 are provided to fit around pins 34, which project from the annular wall 35 of bowl 12 inwardly to serve as a hanger means for bag or elongated container 20 when it occupies arcuate channel 16.

Bag 20 also defines intermediate connection ports for tubing 36 and 37 which are positioned to communicate with sealed chamber portion 26 of the elongated bag or container. Ports for tubing 28, 30, and 37 penetrate the seal 24 in conventional, sealed manner. The connection details for tubing 36 will be described later.

Seal 39 defines a constricted portion inside of the interior of bag 26 to divide it into two segments separated by narrow communicating channel 41 as shown in FIG. 3. This permits, after use, the easy sealing and separation of the bag at constricted channel 41 for harvesting of platelets in one segment thereof.

Figure 5:
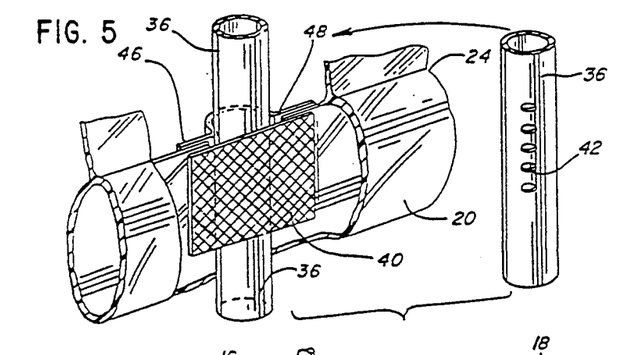
FIG. 5 is a detailed perspective view of an alternate technique for connecting the tubing to the container, with portions broken away.
Figure 6:
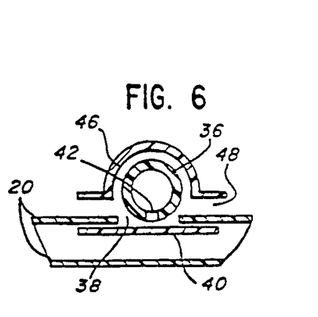
FIG. 6 is a longitudinal sectional view of the connection illustrated in FIG. 5.

A detailed connection system for communication tubing 36 in the elongated bag or container 20 is shown in FIGS. 5 and 6 where, a fragment of the elongated flat container 20 is shown. Container 20 may be made of thin-walled, tubular plastic material, for example polyvinylchloride, among other materials. An aperture 38 is cut in the side wall of bag 20, and is covered by a filter screen 40. The tubing, for example communication tubing 36 (a portion of which is separately shown for clarity in FIG. 5) defines a plurality of perforations 42 in its side wall. The plurality of perforations 42 in the side wall of the tubing are adjacent the filter screen 40 to allow communication between the tubing and the interior of fluid container 20. The ends of tube 36 loop together to form in each case a single connecting tube 44 as shown in FIG. 3.

An outer wall member 46 tightly and sealingly surrounds the portion of tubing 36 containing perforations 42 and which may be R.F. sealed to the cut side wall of tubing 20. In particular, a seal line 48 runs around aperture 38 between outer wall member 46, tube 36 and the cut side wall of bag 20, to provide a seal around aperture 38.

As shown in FIGS. 1 and 2, bag 20 is positioned in annular slot 16, with inlet port 28 projecting outwardly as shown through a space 50 in cover member 14. If desired, cover member 14 may be in two pieces, being separated at both space 50 and at diametrically opposed junction 52, to provide a pair of generally semi-circular cover member sections 53, 55.

Bag or elongated container 20 is inserted into annular channel 16 in a clockwise manner with the inlet tubing 28 positioned at 50, the length of bag 20 being so proportioned that it terminates adjacent the outlet slot 54 in cover member 14, which provides room for the exit of tubing 30. As stated before, pins 34 are placed through perforations 32 of bag 20 to support the bag in the annular slot 16. Bowl member 12 may typically be adapted to rotate in clockwise manner.

In a first segment 54 of arcuate slot 16 approximately defined between the positions of tubes 28 and 36, it will be noted that the respective slot-defining walls of bowl assembly 12 and cover 14 are proportioned to cause the slot to spiral outwardly. As shown in FIG. 1, outer wall 35 of bowl member 12 defines the spiral shape. The spiral curve may be defined by the angle between radius 58 from the center of rotation to the outer wall 35 and the line 57 tangent to the defining curve of outer wall 35 at the intersection with the radius. This angle is designated 56 and for increasing or outwardly directed spirals may range in magnitude from about 80 to 85 degrees (specifically 82 ½ degrees which is preferred for a G field of about 200 to 220 G). This provides a gradually increasing centrifugal force on the blood or other fluid in annular channel 16 during the centrifugal process as it flows along the length of container 20, which causes the red blood cells not only to migrate to the radially-outward wall of elongated bag 20, but also to migrate in a clockwise manner to the end of spiral section 59 of arcuate channel 16. The resultant change in radius may preferably be about 0.2 to 1 cm., specifically about 0.4 cm.. Typically, the blood in first segment 54 of slot 16 may be subjected to continuously changing G fields as it moves along and is confined by the spiral channel varying outwardly by about ten percent of its radius. Generally, this invention may be used to create G fields of about 150 to 1,000 g, to obtain the desired separation and collection of red and white cells at low G fields to avoid the activation of platelets. The optimum angle 56 will change with different G fields.

Alternatively, the angle 56 may be 83 degrees, and the G field is about 285 G at the blood inlet to slot 16.

At the end of spiral section 59, the annular channel 16 defines a radially-inward step 60. Elongated container 20 is so positioned that communication tubing 36 which loops to form connecting tube 44 is positioned at step 60, projecting outwardly through aperture 62 in cover 14.

The red cells are retained in the radially-outward pocket defined by step 60, and may be withdrawn from elongated container 20 through tubing 36. Aperture 38 and screen 40 are placed on the radially-outward lateral side of the elongated container, 20 and collect red blood cells with great efficiency from the pocket defined by step 60.

After the inward step 60, arcuate channel 16 may define a generally circular section 64, which terminates generally in a pocket 66 defined in the vertical arcuate wall 35 of bowl member 12. On centrifugation, elongated container 20 tends to distend into pocket 66, to provide a collection reservoir for white cells, as well as any red cells that have spilled over from the area defined by step 60. Communication tube 37 may be positioned on bag 20 at this point to withdraw the white cells.

Transverse R.F. seal 39 in elongated container 20 is positioned adjacent inwardly positioned outlet 68, which comprises a pair of upstanding, radially inwardly directed walls 70 and a lateral aperture 71 communicating through the annular upstanding wall 74 of cover member 14.

The portion 72 of container 20 which collects platelets is positioned in a section 76 of arcuate channel 16, which may define a generally circular arc, containing the downstream end of the container 20 and outlet tube 30. Generally, upon centrifugation, the platelets gently adhere to the outer wall of portion 72 of elongated container 20, and may be resuspended and stored by agitation within the elongated container itself in a known manner until ready for use.

It has been found to be generally desirable for section 76 of the arcuate channel 16 to be positioned radially inwardly from at least the downstream end of spiral portion 59 of the arcuate channel, to exert on the platelets a somewhat lower centrifugal force than that which has been found to be optimum for the collection of blood cells. By this means, an optimum centrifugal force (such as 200 to 220 G and preferably no more than 400 G) for blood cells can be utilized, while at the same time the platelets do not pack excessively upon the radially outer wall of container 20.

Figure 7:
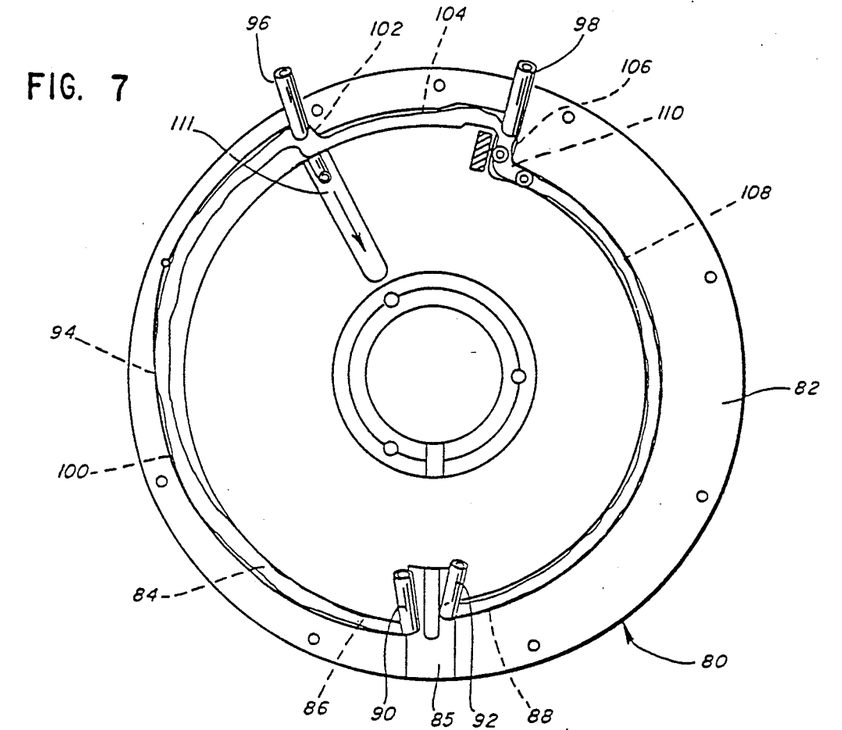
FIG. 7 is a plan view of an alternate embodiment for the centrifuge bowl of this application.

FIG. 7 is a plan view of a variant of the centrifuge bowl of this invention. As in the previous embodiment, bowl 80 includes a cover 82 which cooperatively defines, with bowl 80, an arcuate channel 84. Channel 84 may be interrupted by slot 85 in cover 82 to define a beginning portion 86 and an end portion 88. Access tubing 90 and 92 are carried by an elongated collapsible container 94, similar to bag 20 and positioned within channel 84. Intermediate access tubings 96 and 98 are also carried by bag 94.

As in the previous embodiment, portion 100 of the arcuate channel is outwardly spirally-shaped for the same purpose as the previous embodiment, terminating in a step portion 102 to provide a pocket for the entrapment of red cells. Preferably, the same slot configuration is used as in the previous embodiment, to provide the same order of varying G field. The red cells may then be withdrawn through tubing 96.

Second segment 104 of channel 84 then leads to second step 106, which may be larger than the first step 102, and which is for the purpose of collecting white cells and any residual red cells that may have escaped the previous pocket. The white cells may be withdrawn through tubing 98, connected with container 94.

Third segment 108 of the arcuate channel 84, containing bag 94, then may define a circular arc which is positioned radially inwardly of the entire red cell separating portion 100 of arcuate channel 84, to reduce the G field for platelet separation by collection on the outer wall of bag 94, for example a G field of 120 to 125 G.

After cell separation operations are completed, bag 94 is removed, and may be R. F. sealed to close the bag interior and then severed at area 110, for example, for separation of the platelet-containing portion 108 of the bag for storage, if desired.

As short separation bag may also be used, turning into and terminating at slot 111, for the separation only of red cells and plasma. The outlet tubing then leads from a radially-inward portion of bowl 80.

Figure 8:
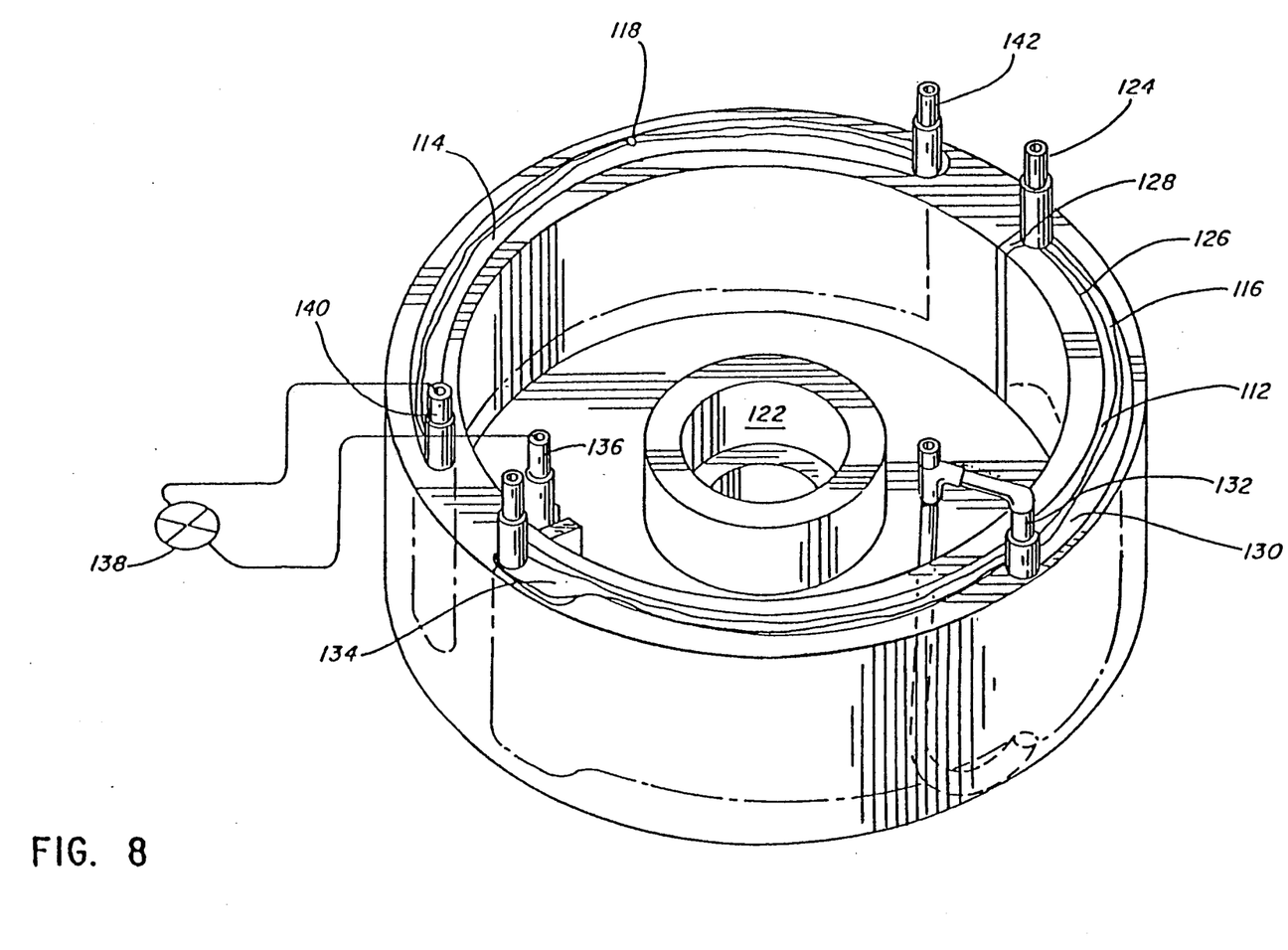
FIG. 8 is a perspective view of a third embodiment of the centrifuge bowl of this application, with one portion shown schematically.

FIG. 8 is a perspective view of another bowl in accordance with this invention. In this embodiment, no cover is used, but a pair of elongated, flexible bags 112, 114, of construction generally similar to bag 20, are provided in a pair of arcuate channels 116, 118 defined in a bowl 120.

As in the previous embodiments, a central aperture is defined by sleeve 122, provided for fitting upon a centrifuge spindle for rotation.

Inlet tubing 124 is connected to one end of bag 112, being supported by radially inwardly positioned walls 126. In this embodiment, slot 116 defines a radially-inward end portion 128, to permit the bag 116 to turn radially inwardly, and then to extend in the circumferential direction through the main portion of slot 116.

A first pocket 130 is defined in the outer surface of slot 116, to serve as an initial red cell collecting pocket. Tubing 132 is positioned on bag 112, to be in communication with the bag interior adjacent the pocket 130, to remove collected red cells. Bag 112 and slot 116 terminate at second pocket 134, from where tubing 136 (shown schematically) communicates between bag 112 and a conventional blood pump 138, for example a roller pump for propelling blood through the system during centrifugation.

Downstream from roller pump 138, tubing 140, which is an extension of tubing 136, communicates with an end of the second bag 114, residing in slot 118 for collection of platelets in bag 114. The resulting platelet-poor plasma is then removed from the other end of bag 114 through tubing 142.

This arrangement eliminates the need for cutting the bags by providing separate, elongated, flexible, collapsible bags for blood cell collection and for the platelets.

White cells will also tend to collect in pocket 134. The entrance of tubing 136 may be positioned only at the top of the bag and at a relatively radially-inward position, if desired, so that the white cells are retained in pocket 134. Otherwise, other appropriate means for collection of the white cells, as in the previous embodiments, may be utilized if desired.

Slot 116 may spiral outwardly, if desired, as in the previous embodiments, or may define a circular arc about the axis of rotation.

The above has been offered for illustrative purposes only, and is not intended to limit the invention of this application, which is as defined in the claims below.

That which is claimed is:

1. The combination of a disposable container and a centrifuge, said combination comprising,
   a rotor;
   means defining a generally annularly extending multi-portion processing channel in said rotor for processing a suspension including at least one cell component;
   said channel including one portion for performing a separation function;
   said channel including another portion for performing another separation function, said other portion being generally spiral-like relative to the true center of said rotor;
   a disposable plastic suspension-receiving container disposed within said one and other portions of said channel; and
   fluid connection means at separated locations of said container for introducing the suspension into and extracting at least one suspension component from said container, said fluid connection means including:
   a first fluid connection means;
     (a) communicating with the part of said container disposed in said other portion of said channel,
     (b) being adapted for extracting a first suspension component from the part of said container disposed in said other portion of said channel, and
     (c) being located at a greater radial distance from the true center of the rotor than the radial distance where the first suspension component enters the part of said container disposed in said other portion of said channel.

2. The combination of claim 1 wherein said fluid connection means further comprises a second fluid connection means communicating with said container at a location spaced from the true center of rotation of said rotor, for introducing the cell-containing suspension into said container, a third fluid connection means communicating with the part of said container disposed in said one portion of said channel for removing a second suspension component from said container, and a fourth fluid connection means communicating with said container at a selected location for removing a third component of the suspension from said container.

3. The combination of claim 1 wherein said container is sufficiently flexible to permit insertion into said one and other portions of said channel.

4. The combination of claim 1 wherein said one portion of said channel is generally circular.

5. The combination of claim 1 wherein said one portion of said channel is arcuate.

6. The combination of claim 1 wherein said channel includes radially inner and outer wall surfaces, and a suspension component receiving pocket is defined by said outer wall surface at a selected location in said channel.

7. The combination of claim 6 wherein said pocket is defined in said one of said portions of said channel.

8. The combination of claim 7 wherein at least one of said fluid connection means communicates with the interior of said container adjacent said pocket for removing from said container the suspension component collected in said pocket.

9. The combination of claim 1 wherein said channel includes radially inner and outer wall surfaces, said outer wall surface of said channel including a transition portion of decreasing radius relative to said true center of said rotor, said transition portion being located between said one and said other portions of said channel and defining a generally inwardly extending surface within said channel to restrict the flow of a suspension component between said one and other portions.

10. The combination of a disposable container and a centrifuge, said combination comprising:
    a rotor;
    means providing a generally annularly extending multiportion processing channel in said rotor for processing a suspension including at least one cell component;
    said channel including one portion for performing a separation function;
    said channel including another portion for performing another separation function, said other portion being generally spiral-like relative to the true center of said rotor;
    said multi-portion processing channel having a total arc that is no greater than 360°;
    a disposable plastic suspension-receiving container disposed within said one and said other portions of said channel; and
    fluid connection means at separated locations of said container for introducing the suspension into and extracting at least one suspension component from said container.

11. The combination of claim 10 wherein said fluid connection means includes a first fluid connection means communicating with the part of said container disposed within said other portion of said channel for removing a first suspension component from said container, a second fluid connection means communicating with said container at a location spaced from the true center of rotation of said rotor, for introducing the cell-containing suspension into said container, a third fluid connection means communicating with the part of said container disposed in said one portion of said channel for removing a second suspension component from said container, and a fourth fluid connection means communicating with said container at a selected location for removing a third component of the suspension from said container.

12. The combination of claim 10 wherein said container is sufficiently flexible to permit insertion into said one and said other portions of said channel.

13. The combination of claim 10 wherein said one portion of said channel is generally circular.

14. The combination of claim 10 wherein said one portion of said channel is arcuate.

15. The combination of claim 10 wherein said channel includes radially inner and outer wall surfaces, and a suspension component receiving pocket is defined by said outer wall surface at a selected location in said channel.

16. The combination of claim 15 wherein said pocket is defined in said one of said portions of said channel.

17. The combination of claim 16 wherein at least one of said fluid connection means communicates with the interior of said container adjacent said pocket for removing from said container the suspension component collected in said pocket.

18. The combination of claim 10 wherein said channel includes radially inner and outer wall surfaces, said outer wall surface of said channel including a transition portion of decreasing radius relative to said true center of said rotor, said transition portion being located between said one and said other portions of said channel and defining a generally inwardly extending surface within said channel to restrict the flow of a suspension component between said one and other portions.

19. The combination of a disposable container and a centrifuge, said combination comprising:
   a rotor;
   means providing a generally annularly extending multiportion processing channel in said rotor for processing a suspension including at least one cell component;
   said channel including one portion for performing a separation function;
   said channel including another portion for performing another separation function, said other portion being generally spiral-like relative to the true center of said rotor;
   said multi-portion processing channel having a total arc that is no greater than 360°;
   a disposable plastic suspension-receiving container disposed within said one and other portions of said channel;
   fluid connection means at separated locations of said container for introducing the suspension and extracting components of the suspension from said container;
   said fluid connection means comprising a first fluid connection for introducing the suspension, a second fluid connection for extracting a first suspension component, a third fluid connection for extracting a second suspension component and a fourth fluid connection means for extracting a third component of the suspension;
   one of said fluid connection means for extracting a suspension component (a) communicating with the part of said container disposed in said other, spiral-like portion of the channel (b) being adapted for extracting a suspension component from said container, and (c) being located at a greater radial distance from the true center of the rotor than the radial distance where the suspension component enters the part of said container disposed in said other, spiral-like portion of said channel.

20. The combination of claim 19 wherein said container is sufficiently flexible to permit insertion into said arcuate and spiral-like portions of said channel.

21. The combination of claim 19 wherein said one portion of said channel is generally circular.

22. The combination of claim 19 wherein said one portion of said channel is arcuate.

23. The combination of claim 19 wherein said channel includes radially inner and outer wall surfaces, and a suspension component receiving pocket is defined by said outer wall surface of said channel.

24. The combination of claim 23 wherein said pocket is defined in said one portion of said channel.

25. The combination of claim 24 wherein at least one of said fluid connection means communicates with the interior of said container adjacent said pocket for removing from said container the suspension component collected in said pocket.

26. The combination of claim 19 wherein said channel includes radially inner and outer wall surfaces, said outer wall surface of said channel including a transition portion of decreasing radius relative to said true center of said rotor, said transition portion being located between said one and said other portions of said channel and defining a generally inwardly extending surface within said channel to restrict the flow of a suspension component between said one and other portions.

27. The combination of claims 1 or 10 wherein said container comprises two plies of thin-wall flexible material defining a flattened tube.

28. The combination of claim 27 wherein said two plies are sealed together to define at least two container segments and a flow path communicating between said segments, said plies being heat sealable at said flow path to permit sealing of said flow path and separation of said container segments.

29. The combination of claim 28 wherein said channel includes a pair of radially inwardly directed walls and said flow path is disposed between said inwardly directed walls.

30. The combination of claim 27 wherein said two plies are sealed together to define a continuously tapered height along at least a portion of said container.

31. The combination of claims 1 or 10 wherein said container includes means defining at least two container segments and a flow path communicating between said segments.

32. The combination of claim 31 wherein said container comprises a plurality of separate spaced apart container segments and a tubing extending between and providing fluid communication between said segments.

33. The combination of claims 1 or 10 wherein said container has a tapered height along at least a portion thereof.

34. The combination of claims 1 or 10 wherein at least one of said fluid communication means comprises:
   means defining an aperture in said container;
   means defining a filter covering said aperture; and
   a fluid conduit communicating with the interior of said container through said filter means.

35. The combination of claim 34 wherein said filter means comprises a filter screen and said fluid conduit comprises a tube attached to said container and having a plurality of perforations therein disposed in direct communication with said filter screen.

36. The combination of claim 34 wherein said fluid conduit comprises a tube extending from opposite sides of said aperture and looping together to provide a single connect tube.

37. The combination of claims 1, 11 or 19 wherein the fluid connection means for removing a suspension component from the part of said container disposed in said other portion of said channel is adapted to remove a cell component of the suspension.

38. The combination of claim 37 wherein the suspension comprises blood and said cell component comprises a blood cell.

39. The combination of claims 2 or 11 wherein said first suspension component substantially comprises a first cell component and wherein said second suspension component substantially comprises a second cell component.

40. The combination of claim 39 wherein the suspension comprises blood and the first and second cell components are blood cells.

41. The combination of claim 40 wherein the third suspension component substantially comprises plasma.

42. The combination of claims 1, 11 and 19 wherein the suspension includes at least one blood cell component.

43. The combination of claims 1, 11 or 19 wherein the suspension comprises blood and said container contains a quantity of blood which is relatively small compared to the volume of blood in a human donor.

44. The combination of claim 1, 10 or 19 wherein said channel is defined by a pair of spaced apart rigid vertical walls, a substantial part of said channel having a height substantially greater than its width along a substantial length of said channel, said channel containing a quantity of blood which is relatively small compared to the volume of blood in a human donor.

45. The centrifuge assembly of claim 1, 10 or 19 wherein said processing channel has a total arc of less than 180°.

* * * * *

UNITED STATES PATENT AND TRADEMARK OFFICE
CERTIFICATE OF CORRECTION

PATENT NO. : 5,217,426
DATED : June 8, 1993
INVENTOR(S) : David V. Bacehowski, et al It is certified that error appears in the above-indentified patent and that said Letters Patent is hereby corrected as shown below:

Column 4, line 36, "cut side" should read --outside--.
Column 4, line 39, "cut side" should read --outside--.
Column 6, line 38, "As" should read --A--.
Column 10, line 52, "communication" should read --connection--.

Signed and Sealed this

Eighth Day of March, 1994

Attest:

BRUCE LEHMAN

Attesting Officer        Commissioner of Patents and Trademarks